United States Patent [19]
Noyori et al.

[11] Patent Number: 5,420,306
[45] Date of Patent: May 30, 1995

[54] PROCESS FOR PRODUCING OPTICALLY ACTIVE GAMMA-BUTYROLACTONE DERIVATIVES

[75] Inventors: Ryoji Noyori; Masato Kitamura, both of Aichi; Takeshi Ohkuma, Gunma; Noboru Sayo; Hidenori Kumobayashi, both of Tokyo, all of Japan

[73] Assignee: Takasago International Corporation, Tokyo, Japan

[21] Appl. No.: 751,843

[22] Filed: Aug. 29, 1991

[30] Foreign Application Priority Data

Aug. 30, 1990 [JP] Japan ................................. 2-228957

[51] Int. Cl.⁶ ........................................... C07D 305/12
[52] U.S. Cl. .................................................. 549/326
[58] Field of Search .......................................... 549/326

[56] References Cited

U.S. PATENT DOCUMENTS

| | | | |
|---|---|---|---|
| 4,892,955 | 1/1990 | Wada et al. | 549/325 |
| 5,021,589 | 6/1991 | Wada et al. | 549/325 |
| 5,079,372 | 1/1992 | Wada et al. | 549/325 |
| 5,349,107 | 9/1994 | Watanabe et al. | 568/318 |

OTHER PUBLICATIONS

J. of Amer. Chem. Soc., vol. 110, No. 2, 20 Jan. 1988, pp. 629–631, Colubus, Ohio, U.S.; M. Kitamura et al: "Homogenous Asymmetric Hydrogenation of Functionalized Ketones".

J. of Amer. Chem. Soc., vol. 109, No. 19, 16 Sep. 1987, pp. 5856–5858, Colubus, Ohio., U.S.; R. Noyori et al.: "Asymmetric Hydrogenation of Beta–Keto Carboxylic Esters. A Practical, Purely Chemical Access to Beta–Hydroxy Esters in High Enantiomeric Purity".

J. of the Chem. Society, Communications No. 2, 1988, pp. 87–88, London, GB; H. Kawano et al.: "Ruthenium (II)-BINAP+ Catalysed Stereoselective Homogeneous Hydrogenation of 1,3-Diketones".

J. of the Chem. Society, Communications No. 13, 1985, 1 Jul. 1985, pp. 922–924, London, GB; T. Ikariya et al.: "Synthesis of Novel Chiral Ruthenium Complexes of 2,2′-Bis(diphenylphosphino)-1,1′-binaphthyl and their Use as Asymmetric Catalysts".

Fieser and Fieser's: "Reagents for Organic Synthesis" vol. 14, 1989, pp. 38–44, John Wiley & Sons, Inc., New York U.S., p. 41, 3rd paragraph—p. 42, first paragraph.

Primary Examiner—C. Warren Ivy
Assistant Examiner—Raymond Covington
Attorney, Agent, or Firm—Sughrue, Mion, Zinn, Macpeak & Seas

[57] ABSTRACT

A process for producing an optically active γ-butyrolactone derivative represented by formula (II):

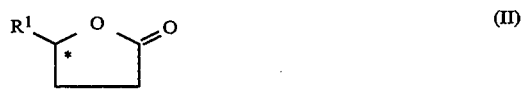

(II)

wherein $R^1$ represents an alkyl group having from 1 to 10 carbon atoms or a substituted or unsubstituted phenyl group; and * indicates an asymmetric carbon atom, is disclosed, comprising enantioselectively hydrogenating a γ-keto acid or an ester thereof represented by formula (I):

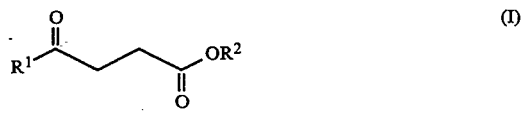

(I)

wherein $R^1$ and * are as defined above; and $R^2$ represents a hydrogen atom or a lower alkyl group, in the presence of an optically active ruthenium-phosphine complex. The compounds (I) can be obtained at high optical purity through simple operations and a reduced number of steps.

6 Claims, No Drawings

PROCESS FOR PRODUCING OPTICALLY ACTIVE GAMMA-BUTYROLACTONE DERIVATIVES

FIELD OF THE INVENTION

This invention relates to a process for producing an optically active γ-butyrolactone derivative which is important as an insect pheromone or a perfume.

BACKGROUND OF THE INVENTION

Many of optically active lactone derivatives represented by formula (II):

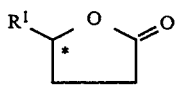
(II)

wherein $R^1$ represents an alkyl group having from 1 to 10 carbon atoms or a substituted or unsubstituted phenyl group; and * indicates an asymmetric carbon atom, are important per se as various insect pheromones or perfumes. Known processes for synthesizing these compounds include (1) a process starting with naturally occurring optically active substances (see Agric. Biol. Chem., Vol. 51, p. 635 (1987)), (2) a process comprising reduction of γ-keto acids by using yeast (see Appl. Microbiol., Vol. 11, p. 389 (1963)), and (3) a process comprising optical resolution of racemates (see JP-A-55-43053, the term "JP-A" as used herein means an "unexamined published Japanese patent application").

With respect to process (3), it is known that racemic γ-butyrolactone is obtained by, for example, hydrogenating maleic acid and/or maleic anhydride in the presence of a ruthenium catalyst, such as a phosphonium chloride, primary to tertiary phosphine hydrochloride or quaternary phosphoniumhydrochloride of ruthenium (see JP-A-2-200680).

Process (1) using a naturally occurring substance as a starting material involves many steps and complicated operations. Process (2) using microorganisms has not yet succeeded to achieve a high optical purity. Process (3) is disadvantageous in that an equivalent amount of an optically active compound is required and that a resolution efficiency reached is poor.

Hence, it has been demanded to establish a process for synthesizing a desired optically active γ-butyrolactone derivative at a higher optical purity through a reduced number of steps.

SUMMARY OF THE INVENTION

In the light of the circumstances stated above, the inventors have conducted extensive investigations and, as a result, found that a lactone derivative of formula (II) having a high optical purity can be obtained through simple operations and a reduced number of steps by enantioselectively hydrogenating a γ-keto acid or an ester thereof in the presence of a relatively cheap optically active ruthenium catalyst and thus completed the present invention.

The process according to the present invention is illustrated by the following reaction scheme:

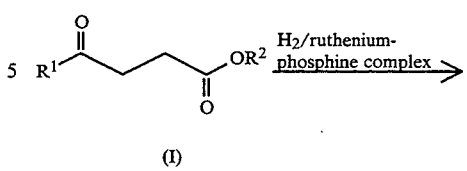
(I)

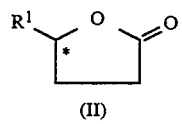
(II)

wherein $R^1$ is as defined above; $R^2$ represents a hydrogen atom or a lower alkyl group (e.g., those having from 1 to 4 carbon atoms); and * indicates an asymmetric carbon atom.

That is, the present invention relates to a process for producing an optically active γ-butyrolactone derivative represented by formula (II), which comprises enantioselectively hydrogenating a γ-keto acid or an ester thereof represented by formula (I) in the presence of an optically active ruthenium-phosphine complex as a catalyst.

DETAILED DESCRIPTION OF THE INVENTION

The γ-keto acid or ester thereof (I) which is used in the present invention as a starting compound can easily be synthesized usually by the process disclosed in Jean Mathieu and Jean Weill-Rayal, *Formation of C-C Bonds*, p. 374, Georg Thieme Publishers, Stuttgart (1979).

Specific examples of the γ-keto acids or esters thereof (I) are levulinic acid, 4-oxohexanoic acid, 4-oxoheptanoic acid, 4-oxodecanoic acid, 4-oxododecanoic acid, 4-phenyl-4-oxobutyric acid, 4-p-methoxyphenyl-4-oxobutyric acid, 4-(3,4-dimethoxyphenyl)-4-oxobutyric acid, 4-(3,4,5-trimethoxyphenyl)-4-oxobutyric acid, and 4-p-chlorophenyl-4-oxobutryic acid, and 4-phenyl-4-oxobutyric acid; and lower alkyl esters thereof, the alkyl moiety of which preferably has from 1 to 4 carbon atoms, such as methyl and ethyl esters.

Optically active ruthenium-phosphine complexes which can be used as a catalyst include:

(1) Compounds represented by formula (III):

wherein $R^3$-BINAP represents a tertiary phosphine represented by formula (IV):

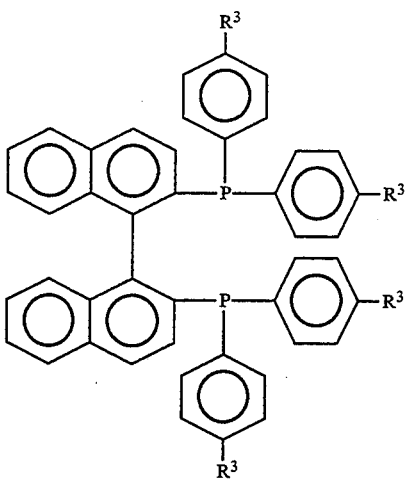

wherein $R^3$ represents a hydrogen atom, a methyl group, or a tert-butyl group; Q represents a tertiary amine; y represents 0 or 1; when y is 0, then x represents 2, z represents 4, and p represents 1; and when y is 1, then x represents 1, z represents 1, and p represents 0;

(2) Compounds represented by formula (V):

wherein $R^3$-BINAP is as defined above; $R^4$ represents a lower alkyl group (e.g., those having from 1 to 4 carbon atoms), a halogenated lower alkyl group (e.g., those having from 1 to 4 carbon atoms), or a phenyl group; and (3) Compounds represented by formula (VI):

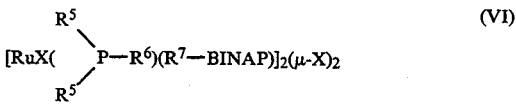

wherein X represents a halogen atom; $R^5$ and $R^6$ which may be the same or different, each represent a substituted or unsubstituted phenyl group; and $R^7$-BINAP represents a tertiary phosphine represented by formula (VII):

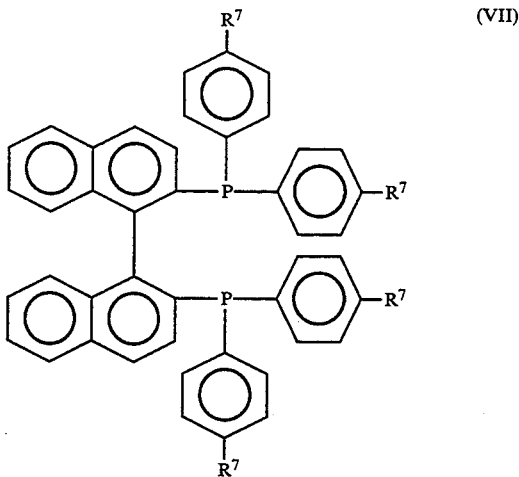

wherein $R^7$ represents a hydrogen atom, a methyl group, a tertbutyl group, or a methoxy group.

The optically active ruthenium-phosphine complexes (1) of formula (III) can be obtained by, for example, the process disclosed in *J. Chem. Soc., Chem. Commun.*, p. 922 (1985) or JP-A61-63690. Specific examples of the complexes (1) are $Ru_2Cl_4(BINAP)_2(NEt_3)$ (wherein BINAP represents 2,2'-bis-(diphenylphosphino)-1,1'-binaphthyl, and Et represents an ethyl group; hereinafter the same), $Ru_2Cl_4(p\text{-}Tol\text{-}BINAP)_2(NEt_3)$ (wherein p-Tol-BINAP represents 2,2'-bis(di-p-tolylphosphino)-1,1'-binaphthyl, hereinafter the same), $RuHCl(BINAP)_2$, and $RuHCl(p\text{-}Tol\text{-}BINAP)_2$.

The optically active ruthenium-phosphine complexes (2) of formula (V) can be obtained by, for example, the process disclosed in JP-A-62-265293. Specific examples of the complexes (2) are:

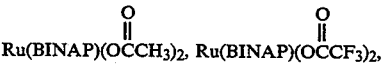

wherein t-Bu represents a tert-butyl group, hereinafter the same), and

wherein Ph represents a phenyl group, hereinafter the same).

The optically active ruthenium-phosphine complexes (3) of formula (VI) can be synthesized from, for example, a rutheniumphosphine complex represented by formula (VIII):

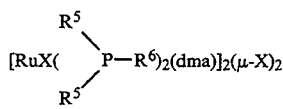

(VIII)

wherein $R^5$, $R^6$, and X are as defined above; and dma represents N,N-dimethylacetamide.

In the ruthenium-phosphine complexes of formulae (VI) and (VIII), $R^5$ and $R^6$, which may be the same or different, each represent a substituted or unsubstituted phenyl group, specific examples of which include a phenyl group; an alkyl-substituted phenyl group, e.g., 2-methylphenyl, 3-methylphenyl, and 4-methylphenyl; an alkoxy-substituted phenyl group, e.g., 2-methoxyphenyl, 3-methoxyphenyl, and 4-methoxyphenyl; and a dialkylaminophenyl group, e.g., 2-dimethylaminophenyl, 3-dimethylaminophenyl, and 4-dimethylaminophenyl.

Of the compounds represented by formula (VIII), for example, the compound wherein $R^5$ and $R^6$ both represent a phenyl group, and X represents a chlorine atom, i.e., [RuCl(PPh$_3$)$_2$-(dma)]$_2$($\mu$-Cl)$_2$, can be quantitatively prepared as follows. [RuCl$_3$(PPh$_3$)$_2$(dma)](dma) which is obtained, e.g., by the process according to I. S. Thorburn, S. J. Rettig, and B. R. James, *Inorg. Chem.*, Vol. 25, pp. 234–240 (1986), is reacted in hexane at 60° to 90° C. for 1 to 20 hours and, after cooling to room temperature, the reaction mixture is filtered through a glass filter, washed with hexane, and dried.

Of the compound represented by formula (VI), the complex wherein $R^5$ and $R^6$ both represent a phenyl group, $R^7$ is a hydrogen atom, and X is a chlorine atom, i.e., [RuCl (PPh$_3$)-(BINAP) ]$_2$($\mu$-Cl)$_2$, can then be obtained quantitatively by reacting the thus obtained [RuCl(PPh$_3$)$_2$(dma)]$_2$($\mu$-Cl)$_2$ complex with BINAP in a solvent, e.g., chlorobenzene, o-dichlorobenzene, methylene chloride, and 1,2-dichloroethane, at 50° to 100° C. for 5 to 20 hours, followed by removing the solvent by distillation under reduced pressure.

The following optically active ruthenium-phosphine complexes included in compounds (3) can also be prepared in the same manner as described above, except for altering the starting material accordingly.

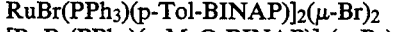
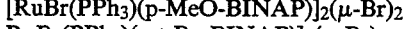
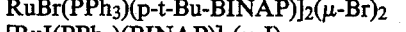
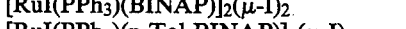
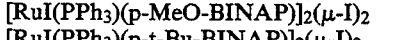
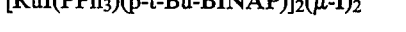

[RuCl(PPh$_3$)(p-Tol-BINAP)]$_2$($\mu$-Cl)$_2$
[RuCl(PPh$_3$)(p-MeO-BINAP)]$_2$($\mu$-Cl)$_2$
[RuCl(PPh$_3$)(p-MeO-BINAP)]$_2$($\mu$-Cl)$_2$
RuBr(PPh$_3$)(BINAP)]$_2$($\mu$-Br)$_2$
RuBr(PPh$_3$)(p-Tol-BINAP)]$_2$($\mu$-Br)$_2$
[RuBr(PPh$_3$)(p-MeO-BINAP)]$_2$($\mu$-Br)$_2$
RuBr(PPh$_3$)(p-t-Bu-BINAP)]$_2$($\mu$-Br)$_2$
[RuI(PPh$_3$)(BINAP)]$_2$($\mu$-I)$_2$
[RuI(PPh$_3$)(p-Tol-BINAP)]$_2$($\mu$-I)$_2$
[RuI(PPh$_3$)(p-MeO-BINAP)]$_2$($\mu$-I)$_2$
[RuI(PPh$_3$)(p-t-Bu-BINAP)]$_2$($\mu$-I)$_2$

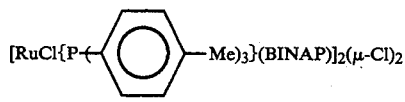

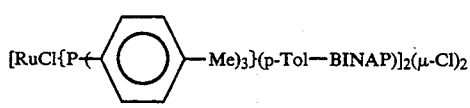

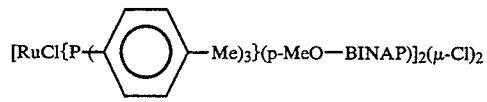

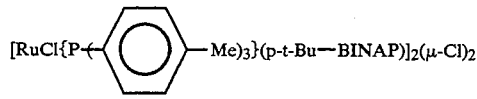

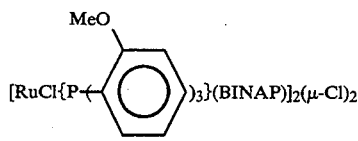

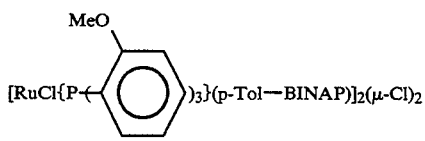

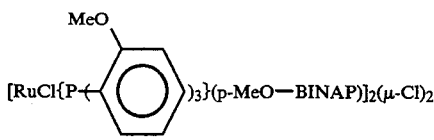

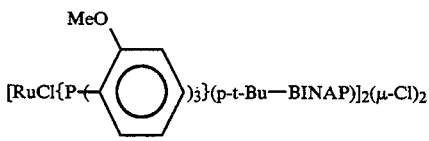

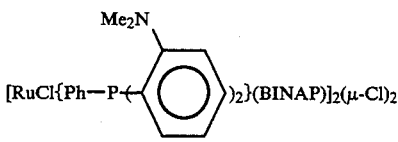

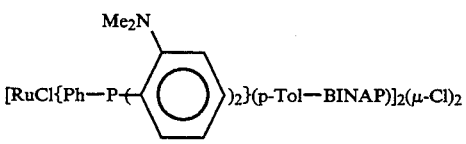

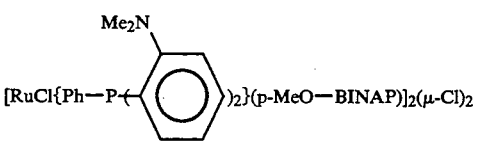

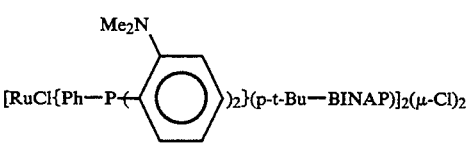

In the above formulae, Ph means a phenyl group; Me means a methyl group; p-Tol-BINAP means 2,2'-bis(di-p-tolylphosphino)-1,1'-binaphthyl; p-MeO-BINAP means 2,2'-bis(di-p-methoxyphenylphosphino)-1,1'-binaphthyl; and p-t-Bu-BINAP means 2,2'-bis(di-p-tert-butylphenylphosphino)-1,1'-binaphthyl.

In carrying out the process of the present invention, a $\gamma$-keto acid or an ester thereof (I) is dissolved in a solvent, the solution is charged in an autoclave, and an optically active ruthenium-phosphine complex is added to the solution in an amount of from 0.01 to 0.001 mole per mole of the γ-keto acid or ester thereof (I) to conduct enantioselective hydrogenation with stirring at a temperature of from 5° to 50° C., and preferably from 25° to 30° C., under a hydrogen pressure of from 5 to 100 kg/cm² for 5 to 300 hours. The product can be isolated from the reaction mixture by removing the solvent and distilling the residue under reduced pressure and/or diluting the residue with a developing solvent, followed by silica gel column chromatography.

The present invention has industrial advantages, providing a process for producing an optically active γ-butyrolactone derivative useful as an insect pheromone or a perfume at a satisfactory optical purity through simple operations and a reduced number of steps.

The present invention is now illustrated in greater detail with reference to Examples, but it should be understood that the present invention is not construed as being limited thereto.

EXAMPLE 1

Synthesis of (R)-4-Methyl-γ-butyrolactone

In a 100 ml autoclave were charged 2.14 g (14.8 mmole) of ethyl levulinate and 14 ml of ethanol, and 21 mg (0.02 mmole) of [RuCl(PPh₃)((R)-BINAP)]₂(μ-Cl)₂ was added to the solution in a nitrogen atmosphere to conduct hydrogenation at 25° C. and at a hydrogen pressure of 100 kg/cm² for 112 hours. After removing the solvent by distillation, the residue was purified by silica gel column chromatography using hexane-diethyl ether as a developing solvent, and the eluate was heated at 130° C. for 4 hours. After cooling to room temperature, the resulting solution was diluted with 4 ml of diethyl ether, washed with 3 ml of a saturated sodium hydrogencarbonate aqueous solution, and dried over anhydrous sodium sulfate. After separating out the anhydrous sodium sulfate by filtration, the filtrate was concentrated under reduced pressure, and the residue was distilled under reduced pressure to obtain 1.3 g (percent yield: 88%) of (R)-4-methyl-γ-butyrolactone.

b.p.: 90°–100° C./25 mmHg $[\alpha]_D^{16}$:+36.8° (c=1.44, CH₂Cl₂) ¹H-NMR (400 MHz, CDCl₃, δ ppm): 1.42 (d, 3H, J=6.4 Hz), 1.84 (ddt, 1H, J=7.9 Hz, J=9.4 Hz, J=12.4 Hz), 2.30–2.50 (m, 1H), 2.50–2.60 (m, 2H), 4.66 (ddq, 1H, J=6.2 Hz, J=6.4 Hz, J=7.9 Hz)

The product was found to have an optical purity of 99.46%ee by gas chromatography using an optically active capillary column under the following conditions (hereinafter the same):
Column: Lipodex® B (produced by Macherey-Nagel Co.); 25 m fused silica
Column Temperature: 150° C.
Column Inlet Temperature: 190° C.
Carrier Gas: helium

EXAMPLE 2

Synthesis of (R)-4-Methyl-γ-Butyrolactone

In a 100 ml autoclave were charged 1.18 g (10 mmole) of methyl levulinate and 15 ml of methanol, and 169 mg (0.1 mmole) of Ru₂Cl₄((R)-BINAP)₂NEt₃ was added thereto in a nitrogen atmosphere to conduct hydrogenation at 50° C. and at a hydrogen pressure of 100 kg/cm² for 20 hours. The reaction mixture was freed of the solvent by distillation and subjected to silica gel column chromatography using hexane-diethyl ether as a developing solvent to remove the catalyst. The eluate was heated at 130° C. for 3 hours, followed by cooling to room temperature. The resulting solution was diluted with 4 ml of diethyl ether, washed with 3 ml of a saturated sodium hydrogencarbonate aqueous solution, and dried over anhydrous sodium sulfate. After separating out the anhydrous sodium sulfate by filteration, the filtrate was concentrated under reduced pressure, and the residue was distilled under reduced pressure to obtain 0.7 g (percent yield: 70%) of (R)-4-methyl-γ-butyrolactone.

Optical Purity: 98 %ee $[\alpha]_D^{16}$:+36.2° (=1.44, CH₂Cl₂)

EXAMPLE 3

Synthesis of (S)-4-Methyl-γ-butyrolactone

In the same manner as in Example 2, except for replacing Ru₂Cl₄((R)-BINAP)₂NEt₃ with Ru₂Cl₄((S)-BINAP)₂NEt₃, 0.7 g (percent yield: 70%) of (S)-4-methyl-γ-butyrolactone was obtained.

Optical Purity: 98 %ee b.p.: 90°–100° C./25 mmHg $[\alpha]_D^{16}$:−36.2° (C=1.44, CH₂Cl₂) ¹H-NMR (400 MHz, CDCl, δ ppm): 1.42 (d, 3H, J=6.4 Hz), 1.84 (ddt, 1H, J=7.9 Hz, J=9.4 Hz, J=12.4 Hz), 2.30–2.50 (m, 1H), 2.50–2.60 (m, 2H), 4.66 (ddq, 1H, J=6.2 Hz, J=6.4 Hz, J=7.9 Hz)

EXAMPLE 4

Synthesis of (S)-4-Phenyl-γ-butyrolactone

In a 100 ml autoclave were charged 1.78 g (10 mmole) of 4-phenyl-4oxobutyric acid and 14 ml of ethanol. A solution separately prepared from 44.9 mg (0.05 mmole) of

double the molar quantity of concentrated hydrochloric acid, and 5 ml of ethanol was added to the above-prepared solution in a nitrogen atmosphere to conduct hydrogenation at 35° C. and at a hydrogen pressure of 70 kg/cm² for 230 hours. To the reaction mixture was added 8 ml of a 10% sodium hydroxide aqueous solution, followed by stirring at 40° C. for 3 hours. After cooling to room temperature, the resulting solution was extracted twice with 30 ml portions of methylene chloride. The organic layer was removed, and the aqueous layer was adjusted to a pH of 4 with a 10% hydrochloric acid aqueous solution and then again extracted thrice with 20 ml portions of methylene chloride. The combined extract was concentrated, and the residue was purified by silica gel column chromatography using hexanediethyl ether as a developing solvent to obtain 1.02 g (percent yield: 63%) of (S)-4-phenyl-γ-butyrolactone.

Optical Purity: 96.7 %ee b.p.: 85°–95° C./0.1 mmHg $[\alpha]_D^{28}$:−31.4° (c=3.88, CHCl₃) ¹H-NMR (400 MHz, CDCl₃, δ ppm): 1.8–3.0 (m, 4H, CH₂CH₂), 5.57 (t, 1H, J=7 Hz, CH), 7.45 (s, 5H, Ph)

EXAMPLES 5 TO 8

Compounds shown in Table 1 below were synthesized in the same manner as in Example 4, except for using the indicated γ-keto acid or ester, changing the reaction conditions (substrate/catalyst molar ratio, temperature, time, and solvent) as shown in Table 1, and changing the hydrogen pressure from 70 kg/cm² to 100 kg/cm².

TABLE 1

| Example No. | Substrate | Product | Yield (%) | Optical Purity (% ee) | Reaction Condition | | | |
|---|---|---|---|---|---|---|---|---|
| | | | | | S/C* | Temp. (°C.) | Time (hr) | Solvent |
| 5 | Ethyl levulinate | (R)-4-Methyl-γ-butyrolactone | 93 | 99.5 | 600 | 25 | 110 | Ethanol |
| 6 | Ethyl 4-oxododecanoate | (R)-4-Octyl-γ-butyrolactone | 90 | 98.1 | 400 | 35 | 118 | Ethanol |
| 7 | Ethyl 4-phenyl-4-oxo-butyrate | (S)-4-Phenyl-γ-butyrolactone | 60 | 96.7 | 350 | 35 | 258 | Ethanol |
| 8 | Methyl 4-(3,4,5-tri-methoxyphenyl)-4-oxo-butyrate | (S)-4-(3,4,5-Trimethoxy-phenyl)-γ-butyrolactone | 50 | 95.5 | 300 | 35 | 240 | Methanol |

Note:
*:The term "S/C" means a substrate/catalyst molar ratio.

While the invention has been described in detail and with reference to specific examples thereof, it will be apparent to one skilled in the art that various changes and modifications can be made therein without departing from the spirit and scope thereof.

What is claimed is:

1. A process for producing an optically active γ-butyrolactone derivative represented by formula (II):

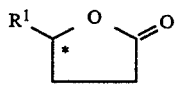
(II)

wherein $R^1$ represents an alkyl group having from 1 to 10 carbon atoms or a substituted or unsubstituted phenyl group; and * indicates an asymmetric carbon atom, which comprises enantioselectively hydrogenating a γ-keto acid or an ester thereof represented by formula (I):

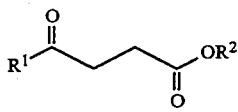
(I)

wherein $R^1$ and * are as defined above; and $R^2$ represents a hydrogen atom or a lower alkyl group, in the presence of an optically active ruthenium-phosphine complex.

2. A process as claimed in claim 1, wherein said optically active ruthenium-phosphine complex is selected from compounds represented by formulae (III), (V), or (VI):

$$Ru_xH_yCl_z(R^3\text{-BINAP})_2(Q)_p \quad (III)$$

wherein $R^3$-BINAP represents a tertiary phosphine represented by formula (IV):

(IV)

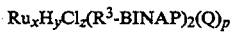

wherein $R^3$ represents a hydrogen atom, a methyl group, or a tert-butyl group; Q represents a tertiary amine; y represents 0 or 1; when y is 0, then x represents 2, z represents 4, and p represents 1; and when y is 1, then x represents 1, z represents 1, and p represents 0,

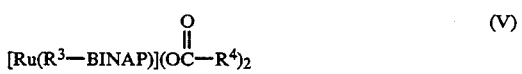
(V)

wherein $R^3$-BINAP is as defined above; $R^4$ represents a lower alkyl group, a halogenated lower alkyl group, or a phenyl group, and

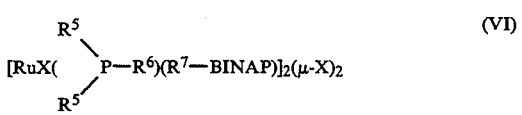
(VI)

wherein X represents a halogen atom; $R^5$ and $R^6$, which may be the same or different, each represent a substituted or unsubstituted phenyl group; $R^7$-BINAP represent a tertiary phosphine represented by formula (VII):

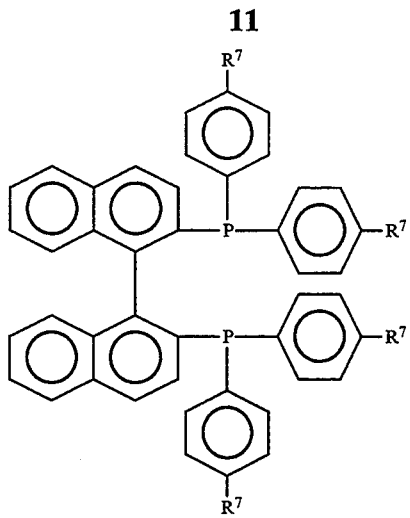
(VII)

wherein $R^7$ represent a hydrogen atom, a methyl group, a tert-butyl group, or a methoxy group.

3. The process as claimed in claim 2, wherein said optically active ruthenium-phosphine complex is a compound represented by formula (VI).

4. The process as claimed in claim 2, wherein said optically active ruthenium-phosphine complex is [RuCl(PPh$_3$)((R)-BINAP)]$_2$($\mu$-Cl)$_2$.

5. The process as claimed in claim 2, wherein said optically active ruthenium-phosphine complex is Ru$_2$Cl$_4$((R)-BINAP)$_2$NEt$_3$.

6. The process as claimed in claim 2, wherein said optically active ruthenium-phosphine complex is Ru((R)-p-Tol-BINAP)(OC(=O)CH$_3$)$_2$.

* * * * *